US012740725B2

(12) United States Patent
Yoo et al.

(10) Patent No.: US 12,740,725 B2
(45) Date of Patent: Sep. 22, 2026

(54) METHOD AND APPARATUS FOR DETECTING STEREOTYPED BEHAVIOR TO SUPPORT DIAGNOSIS OF AUTISM SPECTRUM DISORDER

(71) Applicant: ELECTRONICS AND TELECOMMUNICATIONS RESEARCH INSTITUTE, Daejeon (KR)

(72) Inventors: Cheol-Hwan Yoo, Daejeon (KR); Moon-Ki Back, Daejeon (KR); Jang-Hee Yoo, Daejeon (KR); Byung-Ok Han, Daejeon (KR)

(73) Assignee: ELECTRONICS AND TELECOMMUNICATIONS RESEARCH INSITUTE, Daejeon (KR)

( * ) Notice: Subject to any disclaimer, the term of this patent is extended or adjusted under 35 U.S.C. 154(b) by 237 days.

(21) Appl. No.: 18/660,379

(22) Filed: May 10, 2024

(65) Prior Publication Data

US 2024/0415413 A1 Dec. 19, 2024

(30) Foreign Application Priority Data

Jun. 13, 2023 (KR) ........................ 10-2023-0075242
Mar. 5, 2024 (KR) ........................ 10-2024-0031132

(51) Int. Cl.
*A61B 5/11* (2006.01)

(52) U.S. Cl.
CPC .................................. *A61B 5/1128* (2013.01)

(58) Field of Classification Search
CPC .............................. A61B 5/1128; A61B 5/168
USPC ......................................................... 382/190
See application file for complete search history.

(56) References Cited

U.S. PATENT DOCUMENTS

2009/0060351 A1 3/2009 Li et al.
2015/0146939 A1* 5/2015 Datta .................. A61B 5/7225 382/110
2016/0275336 A1 9/2016 Park et al.
2017/0103264 A1* 4/2017 Javan Roshtkhari .. G06V 20/49
2020/0082939 A1* 3/2020 Dill ........................ G06N 20/00
2021/0209949 A1* 7/2021 Hisanaga ................. G08G 1/16
2022/0233511 A1* 7/2022 Hogenesch .......... A61K 31/436
2022/0319169 A1 10/2022 Sim et al.
2022/0409574 A1* 12/2022 Jing ....................... A61K 36/16
2023/0015295 A1 1/2023 Yun et al.
2024/0257974 A1 8/2024 Wall et al.
2024/0382854 A1* 11/2024 Pedersen ................ A63F 13/67

FOREIGN PATENT DOCUMENTS

KR 10-0791362 B1 1/2008
KR 10-2016-0111268 A 9/2016
KR 10-2008290 B1 8/2019

(Continued)

*Primary Examiner* — Ali Bayat
(74) *Attorney, Agent, or Firm* — LRK PATENT LAW FIRM

(57) ABSTRACT

Disclosed herein is a method for stereotyped behavior detection for supporting diagnosis of Autism Spectrum Disorder (ASD). The method includes detecting a target object to be assessed in an input video, detecting a section in which a periodic behavior occurs using an image sequence of the target object, and classifying a stereotyped behavior in the section in which the periodic behavior occurs.

16 Claims, 8 Drawing Sheets

(56) References Cited

FOREIGN PATENT DOCUMENTS

| | | | |
|---|---|---|---|
| KR | 10-2150623 | B1 | 9/2020 |
| KR | 10-2021-0062256 | A | 5/2021 |
| KR | 10-2022-0004639 | A | 1/2022 |
| KR | 10-2022-0093642 | A | 7/2022 |
| KR | 10-2022-0123885 | A | 9/2022 |

* cited by examiner

METHOD AND APPARATUS FOR DETECTING STEREOTYPED BEHAVIOR TO SUPPORT DIAGNOSIS OF AUTISM SPECTRUM DISORDER

CROSS REFERENCE TO RELATED APPLICATIONS

This application claims the benefit of Korean Patent Applications No. 10-2023-0075242, filed Jun. 13, 2023, and No. 10-2024-0031132, filed Mar. 5, 2024, which are hereby incorporated by reference in their entireties into this application.

BACKGROUND OF THE INVENTION

1. Technical Field

The present disclosure relates to technology for supporting diagnosis of Autism Spectrum Disorder (ASD) through analysis based on Artificial Intelligence (AI).

More particularly, the present disclosure relates to technology for supporting ASD diagnosis through detection of stereotyped behaviors having periodic and repetitive characteristics.

2. Description of Related Art

The Diagnostic and Statistical Manual of Mental Disorders (DSM) published by the American Psychiatric Association defines the characteristics of children with Autism Spectrum Disorder (ASD) as features such as persistent deficits in social interaction and restricted and repetitive behaviors. According to the report by the Centers for Disease Control and Prevention (CDC), the prevalence of ASD children in the United States has increased from one in 54 Children in 2016 to one in 36 children in 2020 and has been continuously increasing every year. In South Korea, the prevalence is one in 38 (2.64%), and a high prevalence and a high growth rate (an average annual growth rate of 6.6%) are observed. Early diagnosis of ASD in children is crucial because it not only provides an opportunity for the child's brain to change into a normal form during the period of high plasticity but also prevents secondary neurological damage and behavioral problems from being accumulated. However, despite the importance of early diagnosis, it is reported that the majority of children are diagnosed with ASD at the age of 6 or older even though symptoms tend to appear between 12 and 24 months, or even earlier.

One of key factors causing the gap between the time of discovering the disorder and the time of diagnosis is the difficulty in accessing ASD assessments. Conventional ASD diagnostic systems rely solely on surveys and clinical observations by specialists, which have a disadvantage of requiring repetition and a long diagnostic time period. Also, the reluctance of parents and children to visit hospitals and undergo diagnosis or long waiting for appointments often leads to missing an early diagnostic opportunity that is crucial for prognosis. Furthermore, because stereotyped behaviors, which are the key behavioral indicators of the above-mentioned features of ASD children, are difficult to diagnose through forced induction by stimuli and occur spontaneously at random times, they are difficult to observe during the limited diagnostic examination time in a hospital, and behavioral patterns that were frequently observed at home are likely not to be observed during a diagnostic assessment due to an unfamiliar examination environment. Also, when conducting parent interviews, medical professionals face limitations in objectively assessing the degree and patterns of symptoms based only on the interviews, without video data or actual observational data. In order to solve the above-mentioned problems, an integrated software framework for estimating the time at which a stereotyped behavior occurs and obtaining a result of recognition of the type of the stereotyped behavior based on an automated analysis system is required.

Conventional technologies used in the behavior detection and recognition fields are optimized for predefined behavior classes and training data, and when behaviors not present in the training data occur in the test condition (open-set settings), which results in a rapid drop in detection performance.

Meanwhile, it is difficult to define representative behavior types due to a wide spectrum of stereotyped behaviors in infants/children, including body stereotypies, such as jumping in place, spinning in place, shaking a head, etc., hand stereotypies, such as flapping hands, clapping hands, etc., and stereotyped use of objects, such as rotating or banging objects. Furthermore, even in the same behavior class, high intra-class variation such as a difference in the time, interval, period, and intensity of each child's behavior makes it difficult to ensure stable detection performance in the final target domain. Also, when it is attempted to detect stereotyped use of objects, target objects include numerous objects such as balls, snacks, paper, peels, dolls, mascaras, and the like, so it is difficult to ensure stable detection performance with existing detectors having predefined object types, such as YOLO (You Only Look Once) or RCNN (Region-based Convolutional Neural Network). In order to solve the above-mentioned problems, a general-purpose detection pipeline capable of detecting all of a wide spectrum of stereotyped behavior patterns and object types is required.

In order to overcome the limitations of the conventional diagnostic protocols and to support early diagnosis of ASD, the present disclosure intends to propose a general-purpose integrated stereotyped-behavior detection method and apparatus capable of estimating a time section in which stereotyped behaviors occur in a long video sequence and recognizing the types of the stereotyped behaviors by automatically analyzing videos, which are obtained through long-term observation and recording of the behaviors of children through a smart CCTV, a webcam, or a camera embedded in a smartphone that can be easily installed in childcare facilities such as homes, kindergartens, and daycare centers, through an AI-based integrated stereotyped behavior detection pipeline.

DOCUMENTS OF RELATED ART (Patent Document 1) Korean Patent No. 0791362, titled "Baby sign recognition method and system and method for interactive multimedia fairytale using the same".

SUMMARY OF THE INVENTION

An object of the present disclosure is to provide an AI-based integrated method for stereotyped behavior detection for supporting diagnosis of children with ASD.

Another object of the present disclosure is to effectively detect repetitive and periodic stereotyped behaviors.

A further object of the present disclosure is to accurately detect subtypes of stereotyped behaviors.

In order to accomplish the above objects, a method for stereotyped behavior detection for supporting diagnosis of Autism Spectrum Disorder (ASD) according to an embodiment of the present disclosure includes detecting a target object to be assessed in an input video, detecting a section in which a periodic behavior occurs using an image sequence of the target object, and classifying a stereotyped behavior in the section in which the periodic behavior occurs.

Here, detecting the section in which the periodic behavior occurs may include detecting a periodic behavior based on first dense sampling for the input video and detecting a periodic behavior based on second dense sampling having a sampling stride that differs from that of the first dense sampling.

Here, detecting the section in which the periodic behavior occurs may comprise determining per-frame periodicity based on a self-similarity matrix generated based on the image sequence of the target object.

Here, detecting the section in which the periodic behavior occurs may comprise determining final per-frame periodicity to be positive when both first per-frame periodicity determined based on the first dense sampling and second per-frame periodicity determined based on the second dense sampling have positive values.

Here, the stereotyped behavior may be classified as a body stereotypy or a hand stereotypy.

Here, classifying the stereotyped behavior may comprise, when the stereotyped behavior is classified as a hand stereotypy, determining whether the hand stereotypy is stereotyped use of an object using a Vision-Language Model (VLM).

Here, the method may further include updating the section in which the periodic behavior occurs when it is determined that stereotyped use of an object is present.

Here, updating the section in which the periodic behavior occurs may comprise updating the section in which the periodic behavior occurs by connecting frames including the object.

Here, detecting the target object may include detecting a human area in the input video and detecting a child area in the detected human area.

Also, in order to accomplish the above objects, an apparatus for stereotyped behavior detection for supporting diagnosis of ASD according to an embodiment of the present disclosure includes an object detection unit for detecting a target object to be assessed in an input video, a periodicity detection unit for detecting a section in which a periodic behavior occurs using an image sequence of the target object, and a stereotyped behavior detection unit for classifying a stereotyped behavior in the section in which the periodic behavior occurs.

Here, the periodicity detection unit may detect a periodic behavior based on first dense sampling for the input video and detect a periodic behavior based on second dense sampling having a sampling stride that differs from that of the first dense sampling.

Here, the periodicity detection unit may determine per-frame periodicity based on a self-similarity matrix generated based on the image sequence of the target object.

Here, the periodicity detection unit may determine final per-frame periodicity to be positive when both first per-frame periodicity determined based on the first dense sampling and second per-frame periodicity determined based on the second dense sampling have positive values.

Here, the stereotyped behavior may be classified as a body stereotypy or a hand stereotypy.

Here, when the stereotyped behavior is classified as a hand stereotypy, the stereotyped behavior detection unit may determine whether the hand stereotypy is stereotyped use of an object using a Vision-Language Model (VLM).

Here, the periodicity detection unit may update the section in which the periodic behavior occurs when it determines that stereotyped use of an object is present.

Here, the periodicity detection unit may update the section in which the periodic behavior occurs by connecting frames including the object.

Here, the object detection unit may detect a human area in the input video and detect a child area in the detected human area.

BRIEF DESCRIPTION OF THE DRAWINGS

The above and other objects, features, and advantages of the present disclosure will be more clearly understood from the following detailed description taken in conjunction with the accompanying drawings, in which.

DESCRIPTION OF THE PREFERRED EMBODIMENTS

Figure 1:
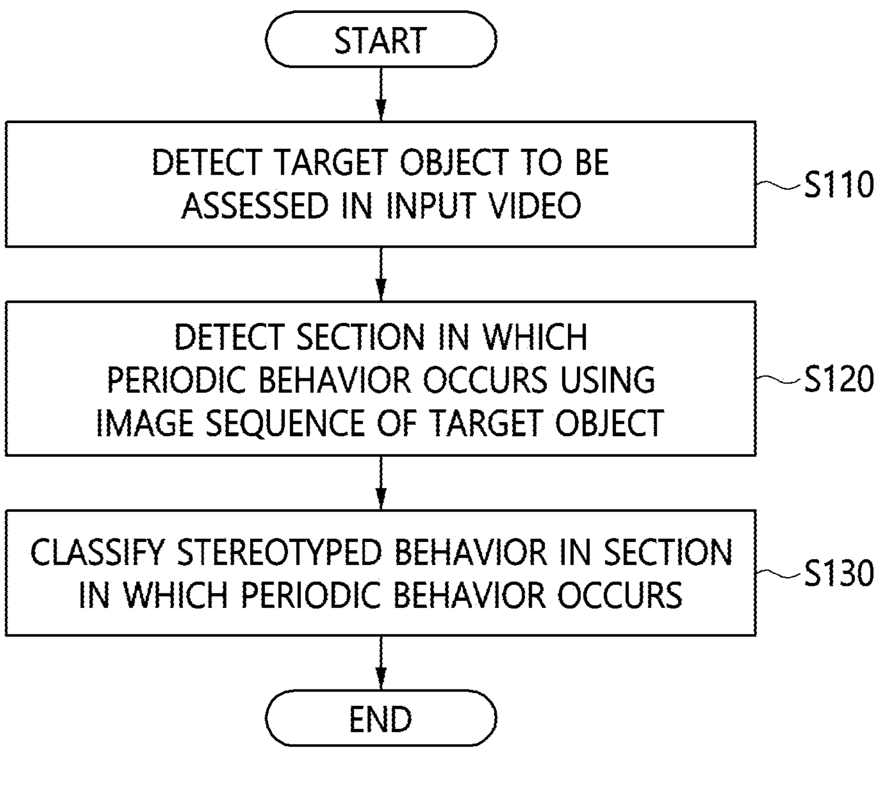
FIG. 1 is a flowchart illustrating a method for stereotyped behavior detection for supporting ASD diagnosis according to an embodiment of the present disclosure.

The advantages and features of the present disclosure and methods of achieving them will be apparent from the following exemplary embodiments to be described in more detail with reference to the accompanying drawings. However, it should be noted that the present disclosure is not limited to the following exemplary embodiments, and may be implemented in various forms. Accordingly, the exemplary embodiments are provided only to disclose the present disclosure and to let those skilled in the art know the category of the present disclosure, and the present disclosure is to be defined based only on the claims. The same reference numerals or the same reference designators denote the same elements throughout the specification.

It will be understood that, although the terms “first,” “second,” etc. may be used herein to describe various elements, these elements are not intended to be limited by these terms. These terms are only used to distinguish one element from another element. For example, a first element discussed below could be referred to as a second element without departing from the technical spirit of the present disclosure.

The terms used herein are for the purpose of describing particular embodiments only and are not intended to limit the present disclosure. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

In the present specification, each of expressions such as "A or B", "at least one of A and B", "at least one of A or B", "A, B, or C", "at least one of A, B, and C", and "at least one of A, B, or C" may include any one of the items listed in the expression or all possible combinations thereof.

Unless differently defined, all terms used herein, including technical or scientific terms, have the same meanings as terms generally understood by those skilled in the art to which the present disclosure pertains. Terms identical to those defined in generally used dictionaries should be interpreted as having meanings identical to contextual meanings of the related art, and are not to be interpreted as having ideal or excessively formal meanings unless they are definitively defined in the present specification.

Hereinafter, embodiments of the present disclosure will be described in detail with reference to the accompanying drawings. In the following description of the present disclosure, the same reference numerals are used to designate the same or similar elements throughout the drawings, and repeated descriptions of the same components will be omitted.

FIG. 1 is a flowchart illustrating a method for stereotyped behavior detection for supporting ASD diagnosis according to an embodiment of the present disclosure.

The method for stereotyped behavior detection for supporting ASD diagnosis according to an embodiment of the present disclosure may be performed by a stereotyped behavior detection apparatus such as a computing device, a server, or the like.

Referring to FIG. 1, the method for stereotyped behavior detection for supporting ASD diagnosis according to an embodiment of the present disclosure includes detecting the target object to be assessed in an input video at step S110, detecting a section in which a periodic behavior occurs using an image sequence of the target object at step S120, and classifying a stereotyped behavior in the section in which the periodic behavior occurs at step S130.

Here, detecting the section in which the periodic behavior occurs at step S120 may include detecting a periodic behavior based on first dense sampling for the input video and detecting a periodic behavior based on second dense sampling having a sampling stride that differs from that of the first dense sampling.

Here, detecting the section in which the periodic behavior occurs at step S120 may comprise determining per-frame periodicity based on a self-similarity matrix generated based on the image sequence of the target object.

Here, detecting the section in which the periodic behavior occurs at step S120 may comprise determining the final per-frame periodicity to be positive when both first per-frame periodicity determined based on the first dense sampling and second per-frame periodicity determined based on the second dense sampling have positive values.

Here, the stereotyped behavior may be classified as a body stereotypy or a hand stereotypy.

Here, classifying the stereotyped behavior at step S130 may comprise, when the stereotyped behavior is classified as a hand stereotypy, determining whether the hand stereotypy is stereotyped use of an object using a Vision-Language Model (VLM).

Here, the method may further include, when it is determined that stereotyped use of an object is present, updating the section in which the periodic behavior occurs.

Here, updating the section in which the periodic behavior occurs may comprise updating the section in which the periodic behavior occurs by connecting frames including the object.

Here, detecting the target object at step S110 may include detecting a human area in the input video and detecting a child area in the detected human area.

Hereinafter, an embodiment of the present disclosure will be described in more detail with reference to FIGS. 2 to 7.

Figure 2:
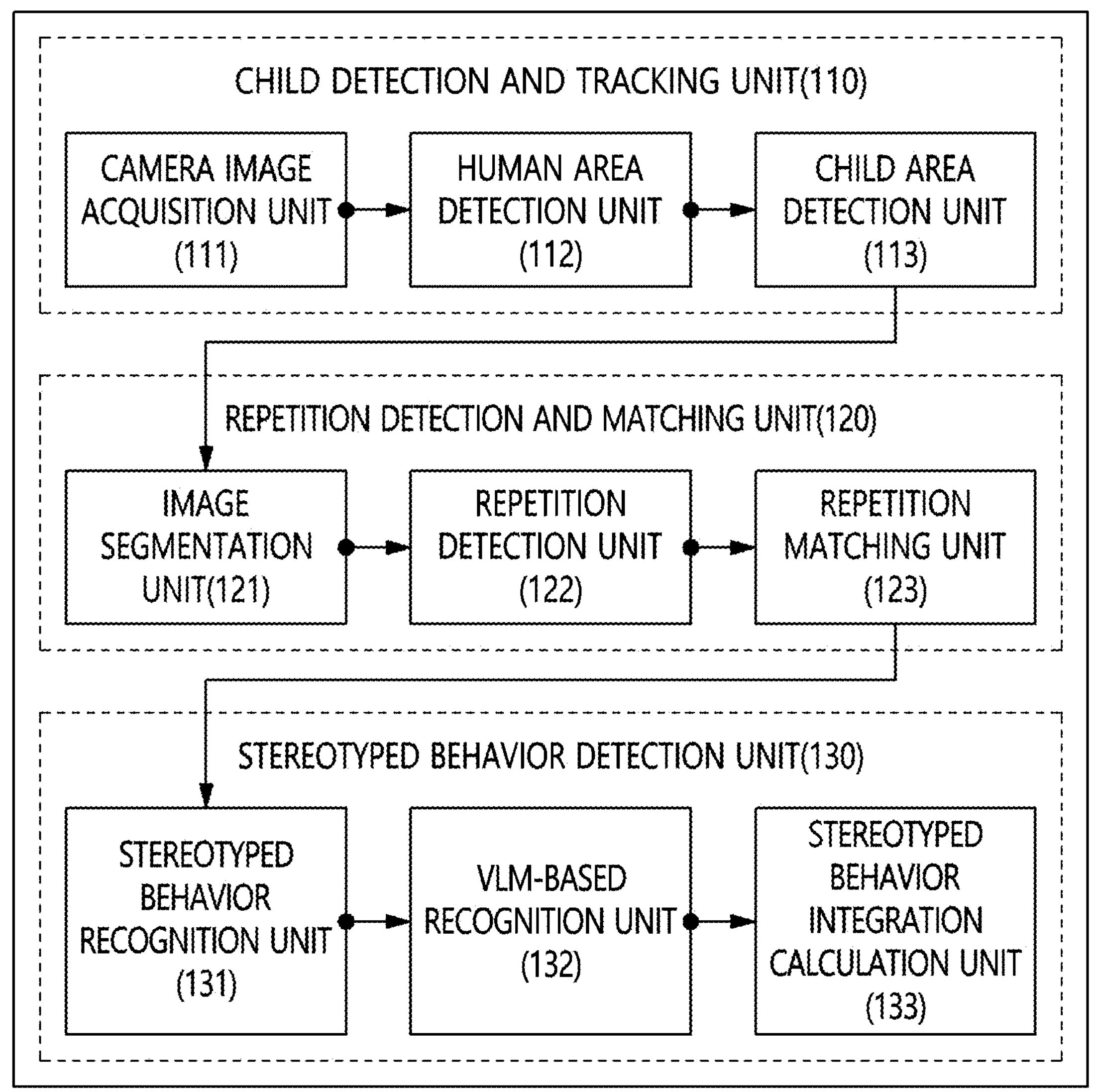
FIG. 2 is a detailed structure diagram of a stereotyped behavior detection pipeline according to an embodiment of the present disclosure.

FIG. 2 is a detailed structure diagram of a stereotyped behavior detection pipeline according to an embodiment of the present disclosure.

Referring to FIG. 2, the integrated pipeline for stereotyped behavior detection according to an embodiment of the present disclosure may include a child detection and tracking unit 110, a repetition detection and matching unit 120, and a stereotyped behavior detection unit 130.

Here, the child detection and tracking unit 110 may include a camera image acquisition unit 111 for receiving video data recording the behavior of a child from a smart CCTV, a webcam, a camera installed in a smartphone, or the like, a human area detection unit 112 for detecting a human area in the input video, and a child area detection unit 113 for detecting an infant/child area in the video based on information about the detected human area.

The repetition detection and matching unit 120 may include an image segmentation unit 121 for splitting the video into multiple clips for a video sequence corresponding to the detected child area, a repetition detection unit 122 for detecting a section in which repetition and periodicity occur in each of the clips, and a repetition matching unit 123 for aggregating the clip-level repetition/periodicity detection results.

Also, the stereotyped behavior detection unit 130 may include a stereotyped behavior recognition unit 131 for recognizing the subtype (body, hand) of a stereotyped behavior by receiving each of the detected behavior sections, a VLM-based recognition unit 132 for additionally determining whether a child is using an object through zero-shot inference based on a Vision-Language Model (VLM), and a stereotyped behavior integration calculation unit 133 for calculating the result of behavior recognition at a video level by aggregating the sections in which the stereotyped behavior occurs in the video and the type and result of the stereotyped behavior in each of the sections.

Hereinafter, the components of the integrated pipeline for stereotyped behavior detection according to an embodiment of the present disclosure will be described in detail.

The child detection and tracking unit 110 may detect a human area in each frame of the video data input from a camera and detect an area including a child in the video based on the detected human area.

The camera image acquisition unit 111 may deliver untrimmed video acquired by observing, capturing, and recording the behavior of a child in an unconstrained condition for a long period of time using a CCTV, a webcam, a camera installed in a smartphone, or the like, which can be easily installed in childcare facilities such as homes, kindergartens, and daycare centers, to the human area detection unit 112.

The human area detection unit 112 may detect a human area in each of the frames of the video received from the camera image acquisition unit 111 using a known object detector, such as YOLO, RCNN, or the like, or may perform human detection using a human pose inference technique for detection robust to the angle of a camera, the position of a body, occlusion, or the like.

To this end, algorithms such as OpenPose, HigherHRNet, and the like based on a bottom-up approach may be used, and a Region of Interest (ROI) is set by selecting the minimum and maximum coordinates, among 2D coordinates based on the detected pixel coordinate system, whereby multiple human areas may be stably detected.

The child area detection unit 113 may serve to detect a child area, which is a target to which attention has to be paid, in the image, which may include not only multiple children but also adults, based on information about the human area detected by the human area detection unit 112. When the human area detection unit 112 uses an object detector, each of the detected areas may be classified as an area corresponding to an adult or a child through an additional recognition process based on age estimation, face verification, or the like, whereas when the human area detection unit 112 uses a human-pose-based detection method, the lengths of bones in the inferred human pose are calculated and compared with a specific threshold value, whereby an adult area or a child area may be identified.

The repetition detection and matching unit 120 serves to receive an image sequence corresponding to the child area detected by the child detection and tracking unit 110 and detect a time section in which repetition or periodicity occurs in the sequence (periodicity detection).

Figure 3:
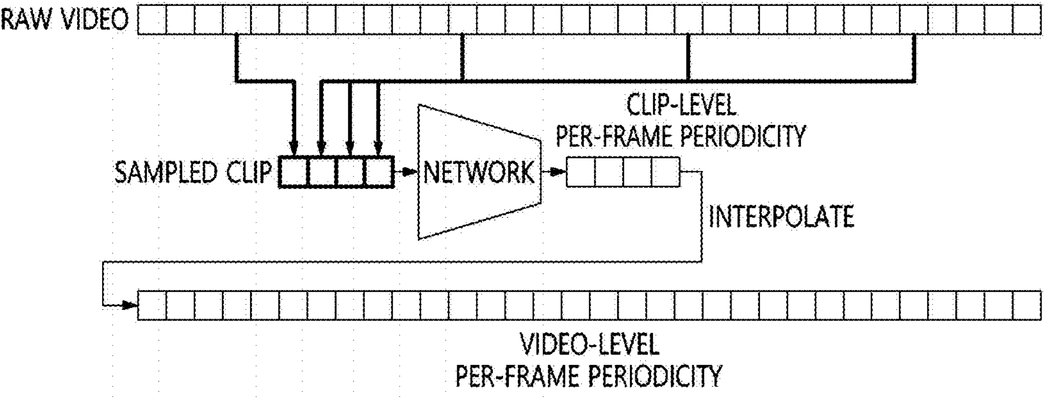
FIG. 3 is an example of a method for detecting repetition and periodicity based on AI.

FIG. 3 is an example of a method for detecting repetition and periodicity based on AI.

In order to perform AI operations in available GPU memory, as in the example of FIG. 3, conventional AI-based repetition and periodicity detection techniques typically sample frames through uniform sampling for a long untrimmed video, predict per-frame periodicity through deep-learning network inference by receiving the sampled video, interpolate the samples to match the original video length, and finally detect a section in which repetition and periodicity occur, as widely used in the existing behavior recognition fields.

Here, uniform sampling is suitable for a behavior recognition task for describing behaviors, such as 'sit', 'stand', or 'run', and extracting features using only key frames, but is not suitable for a task for accurately detecting a section in which repetition and periodicity occur in a video including various periods. For example, when all of the frames that are sampled by uniform sampling for detection of a repeated action such as 'repeatedly sitting down and standing up' are frames capturing a sitting posture, the task of detecting a repetitive section becomes useless. In order to overcome the limitations of the above-mentioned conventional techniques, the present disclosure proposes an inference method based on dense sampling.

Figure 4:
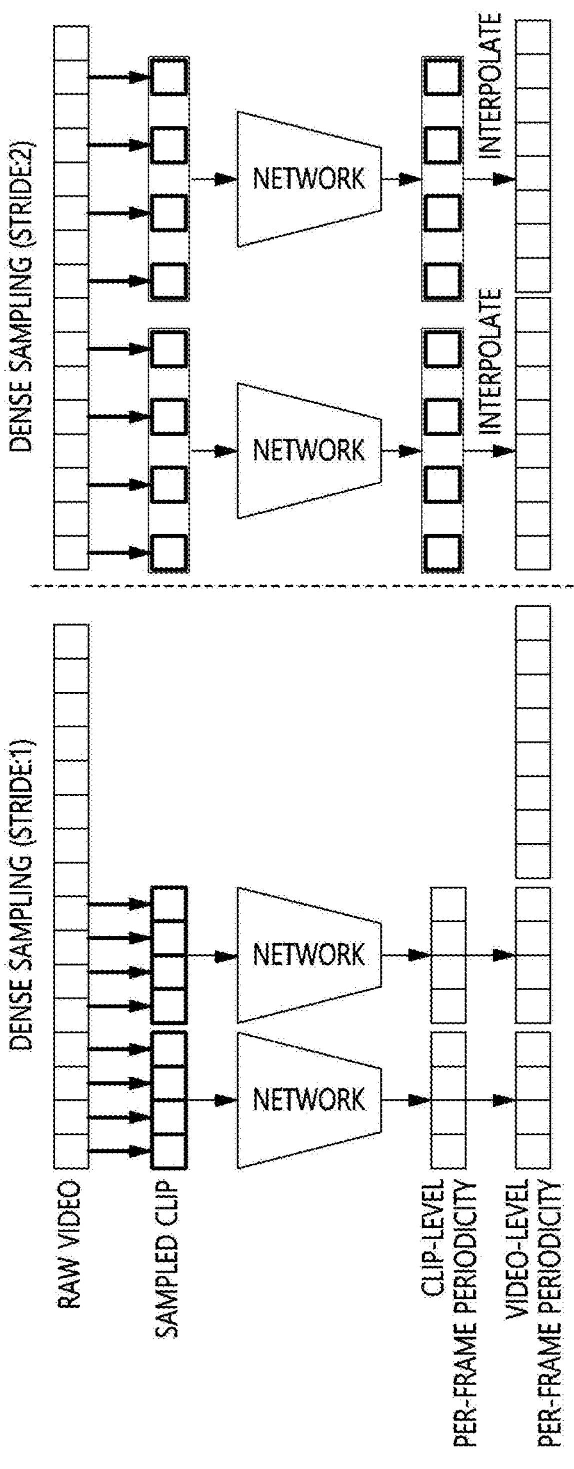
FIG. 4 is an example of a method for detecting repetition and periodicity according to an embodiment of the present disclosure.

FIG. 4 is an example of a method for detecting repetition and periodicity according to an embodiment of the present disclosure.

In the method according to an embodiment of the present disclosure, continuous frames are extracted through dense sampling in order to solve the above-mentioned problem, per-frame periodicity is detected by inputting the continuous frames to a deep-learning network, and a final video-level result is calculated by concatenating inference values. However, unlike the existing uniform sampling method, the dense-sampling-based method has the possibility to act as a disadvantage for a repeated behavior having a long period that requires long-term dependency between frames. Therefore, in the method proposed in the present disclosure, respective results inferred by setting different sampling strides in dense sampling are collected, whereby all of a repetitive behavior having a short period and a repetitive behavior having a long period may be detected in consideration of both the short-term dependency and the long-term dependency. The proposed method may be applied also to a training step in the same manner. In the present disclosure, two stride levels, stride 1 and stride 2, are set in consideration of both experimental observation and computational complexity, and an AND operation may be used to collect the inferred results. However, the stride levels may be variously set to include three or four levels depending on the resource environment in which the method according to an embodiment is performed.

Based on the above-described method, the image segmentation unit 121 performs sampling on the input video, whereby sub-clips having the maximum length (e.g., 300 frames) within available GPU memory are generated (sampled). For example, when the stride is 1, the sampling may be performed on 300 frames of the original video, whereas when the stride is 2, the sampling may be performed on 600 frames of the original video.

The repetition detection unit 122 may infer per-frame periodicity in each of the sub-clips sampled by the image segmentation unit 121 through network inference based on deep learning.

Figure 5:
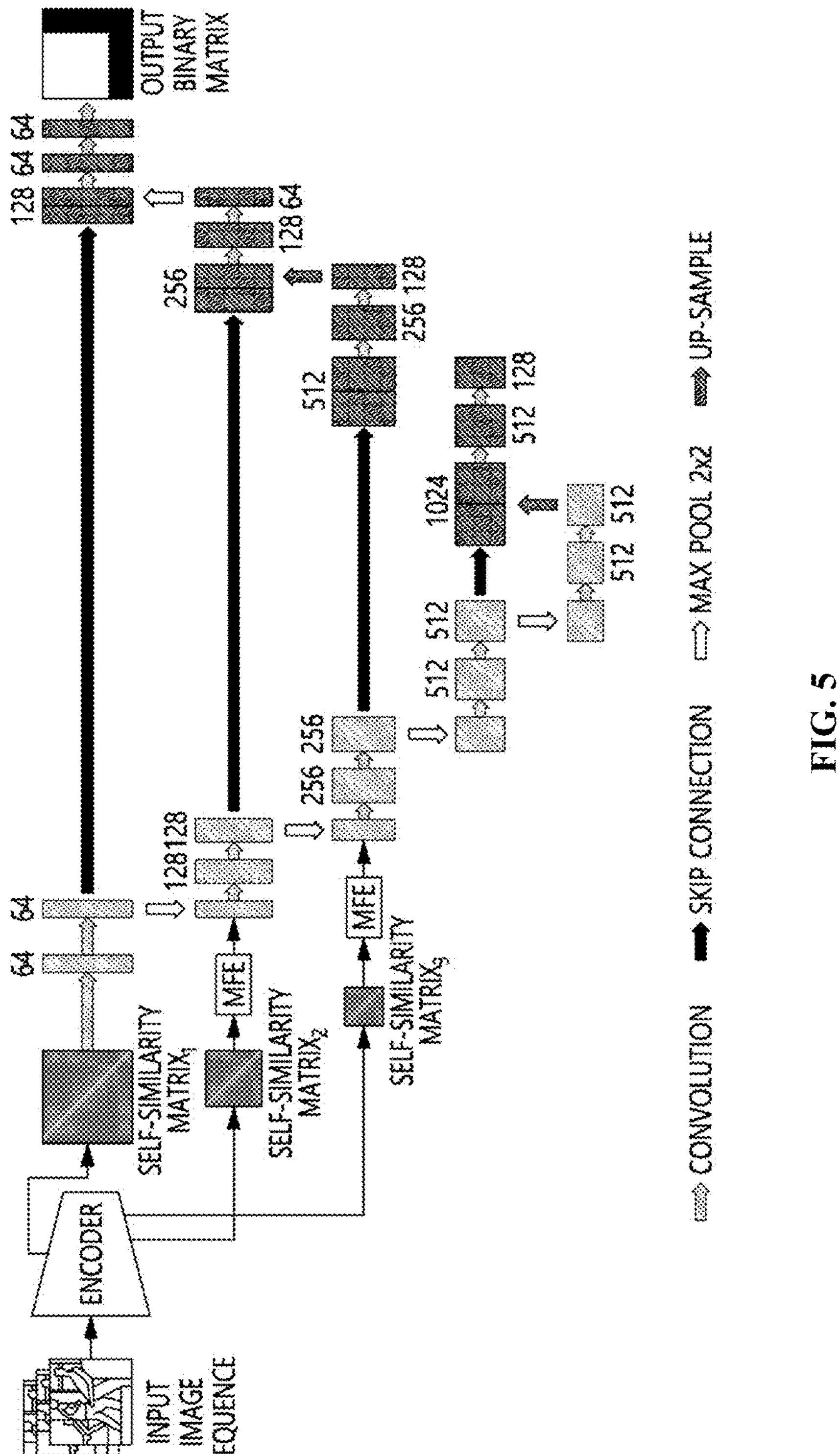
FIG. 5 is an example of a structure diagram of a network for detecting repetition and periodicity in a method according to an embodiment of the present disclosure.

FIG. 5 is an example of a structure diagram of a network for detecting repetition and periodicity in a method according to an embodiment of the present disclosure.

In the present disclosure, given the input image sequence, each frame is embedded into a latent feature using an encoder, as shown in FIG. 5, after which a self-similarity matrix (SSM) is generated by comparing the similarity between the features. Here, as the encoder for extracting the latent feature from each frame, not only a network such as a ResNet based on a 2D CNN but also a network such as an RNN, a 3D CNN, Video Swin Transformer (VST), or the like for processing time-series data in consideration of the interrelationship between frames may be used. In the present disclosure, a 3D ResNet-18 is used as the encoder. Also, in order to use temporal information of various scales, features are extracted from different layers of the encoder, whereby a multi-scale self-similarity matrix is generated. The self-similarity matrix is made pass through a multi-scale feature ensemble (MFE) module and is then used as the input of U-Net, and an argmax operation is performed on the diagonal elements of a finally inferred output binary matrix, whereby per-frame periodicity may be determined.

The repetition matching unit 123 serves to collect clip-level per-frame periodicity inferred by the above-described image segmentation unit 121 and the repetition detection unit 122. In the present disclosure, inference is performed for two levels including stride 1 and stride 2, and an AND operation is performed on the inference results at the respective stride levels in order to ensemble the results. When the per-frame periodicity is classified as positive in all of the stride operations, the final video-level per-frame periodicity is also classified as positive.

Unlike the convention behavior detection techniques that detect action or non-action sections based on predefined and learned behavior types, the method proposed by the present disclosure uses the characteristics of stereotyped behaviors, that is, repetition and periodicity, thereby ensuring stable detection performance even when a repetitive behavior occurs in open-set settings in which the type of the behavior is not present in training data.

The stereotyped behavior detection unit 130 recognizes a subtype of a stereotyped behavior by receiving each section that is detected by the module as a section in which repetition or periodicity occurs in the video.

Specifically, the stereotyped behavior recognition unit 131 receives each of the detected video sections and classifies the type of a stereotyped behavior. In the present disclosure, stereotyped behaviors are broadly classified into binary classes, including body stereotypies (jumping in place, rotating in place, and shaking a head) and hand stereotypies (snapping fingers and flapping hands), which are determined to be representative types of stereotyped behaviors through discussion with medical professionals. As the deep-learning network for video recognition, not only a 3D-CNN-based algorithm, such as Convolutional 3D (C3D), Inflated 3D ConvNet (I3D), or R(2+1)D, but also transformer-based TimesFormer or Video Swin Transformer (VST), which are recent models ensuring high performance, may be used, and in the present disclosure, I3D is used as the classifier.

When the result of recognition by the stereotyped behavior recognition unit 131 is classified as a hand stereotypy, the VLM-based recognition unit 132 analyzes whether a child performs a stereotyped behavior using an object through additional determination. Existing object detectors, such as YOLO, RCNN, and the like, which are widely used for object detection, have limited detection performance depending on predefined object types and training data. For example, a COCO dataset frequently used for training the existing object detectors has a limitation in that it cannot ensure stable detection performance for object types not present in the training data in which about 80 object classes, such as humans, bicycles, cars, motorcycles, and the like, are predefined.

However, when a child shows a stereotyped behavior pattern, the objects that the child can use include any of numerous objects such as balls, snacks, paper, peels, dolls, mascaras, and the like, so a universal extensible detection algorithm capable of detecting all of these unpredictable objects is required. To this end, the present disclosure uses zero-shot inference based on a Vision-Language Model (VLM), such as Contrastive Language-Image Pre-training (CLIP), Grounded Language-Image Pre-training (GLIP), Self-supervision meets Language-Image Pre-training (SLIP), or Bootstrapping Language-Image Pre-training (BLIP), and because the vision-language model is trained with billions of image-text pairs on the Internet through a contrastive learning method, similarity is compared by merely inputting a text prompt at the inference step, without additional training for the target domain, whereby zero-shot inference may be performed.

Particularly, the present disclosure uses CLIP trained with about 400 millions of image-text pairs and compares the similarity between a text prompt list such as [A baby is holding an object in his/her hand, A baby is not holding an object in his/her hand] and an input image for each frame of the input video, thereby determining whether a child is holding an object in his/her hand. When the stereotyped behavior recognition unit 131 classifies the behavior of a child as a hand stereotypy and when it is determined that the child is holding an object in his/her hand using the result obtained from the corresponding VLM model, it is finally determined that an object usage stereotypy occurred. Besides zero-shot classification, a zero-shot Visual Question Answering (VQA) task may also be used for detecting an object usage stereotypy by inputting a question such as [Is a baby holding an object in his/her hand?] using a VLM such as BLIP.

Also, when an object usage stereotypy is finally detected, a time section in which repetition and periodicity occur in the video is updated based on the corresponding result. Training datasets such as Countix, PERTUBE, QUVA, and the like used for training the repetition detection unit 122 mostly include human's repetitive actions with bare hands, and it is difficult to expect stable detection of sections including object usage stereotypies in an inference step. Also, in the case of occlusion by an object in the video, the accuracy of inference of the stereotyped behavior section based on the behavior of a child is inevitably degraded. Therefore, the respective frames capturing hands holding an object, which are determined by the VLM-based recognition unit 132, are connected as a single continuous segment, whereby the previously inferred section in which repetition or periodicity occurs is refined.

Finally, the stereotyped behavior integration calculation unit 133 collects the stereotyped behavior recognition results of the detected sections, thereby calculating a video-level behavior recognition result for the entire video, and in the present disclosure, an average operation is used for simplicity of the algorithm.

Figure 6:
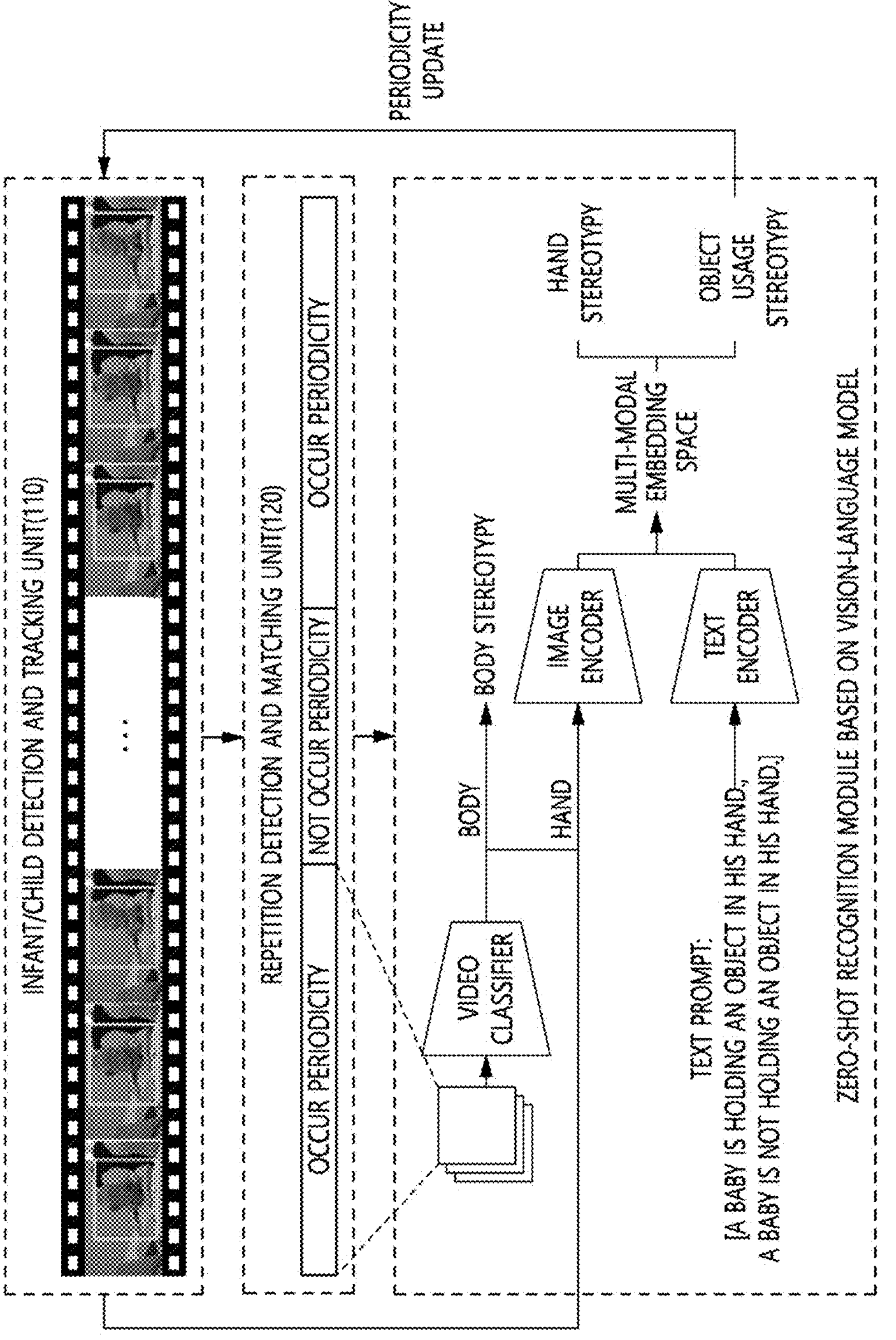
FIG. 6 is an embodiment of an integrated pipeline for detecting stereotyped behaviors.

FIG. 6 is an embodiment of an integrated pipeline for detecting stereotyped behaviors.

Referring to FIG. 6, the operation methods of the infant/child detection and tracking unit 110, the repetition detection and matching unit 120, and the stereotyped behavior detection unit 130 can be understood.

Figure 7:
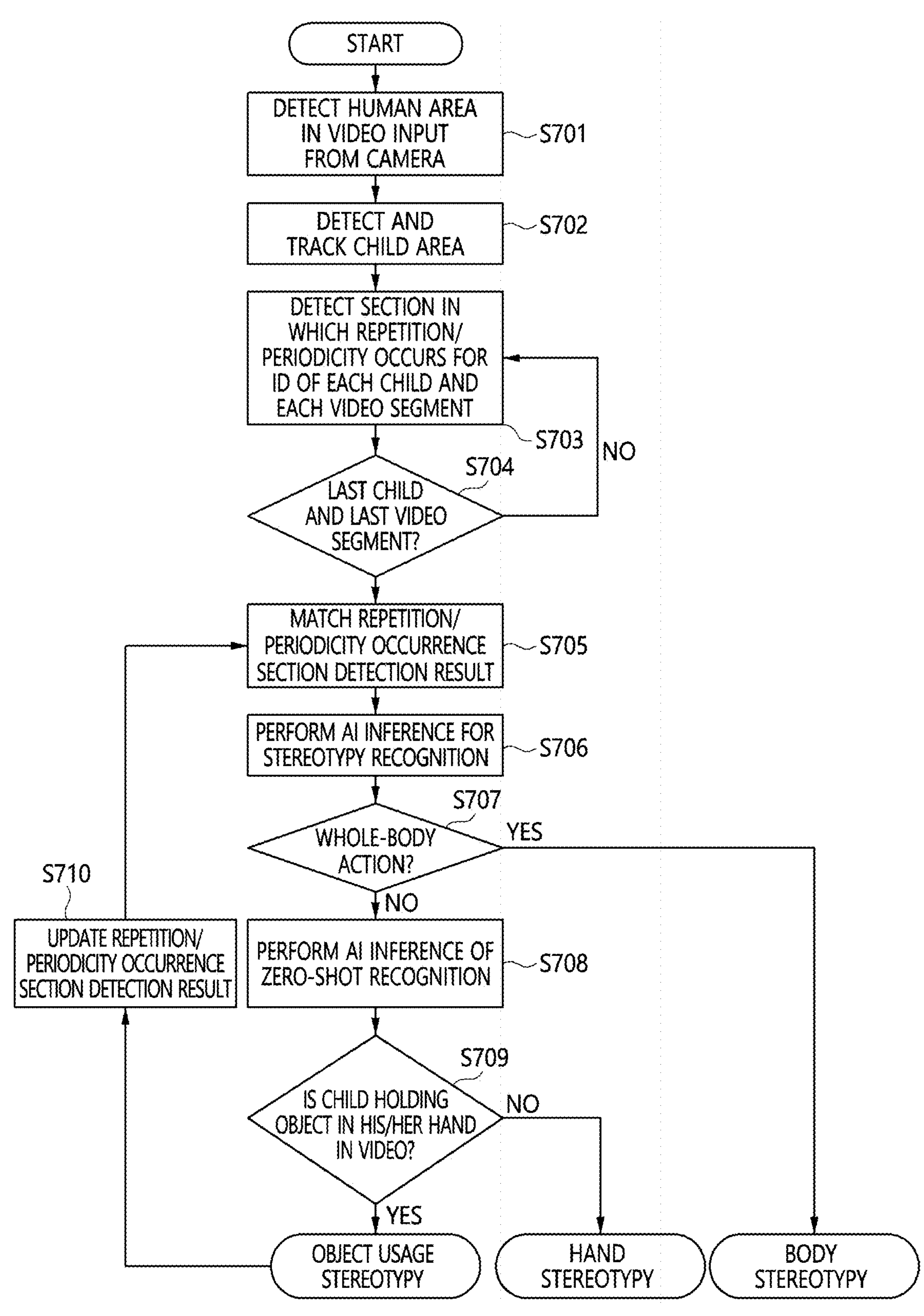
FIG. 7 is a flowchart illustrating in detail a method for stereotyped behavior detection for supporting ASD diagnosis according to an embodiment of the present disclosure.

FIG. 7 is a flowchart illustrating in detail a method for stereotyped behavior detection for supporting ASD diagnosis according to an embodiment of the present disclosure.

Referring to FIG. 7, in the method according to an embodiment, first, a human area is detected in each frame of video data input from a camera at step S701. Through additional recognition for each of the detected human areas, a child area is detected and an identifier (ID) of each child is assigned thereto at step S702. For an image sequence corresponding to the child area of each ID, the video is split into sub-clips corresponding to the maximum number of frames in available GPU memory, after which repetition and periodicity are inferred for each of the sub-clips at step S703.

The corresponding operation is repeated until the last sub-clip of the ID corresponding to the last child at step S704, and after the operation is terminated, the clip-level repetition/periodicity detection results are matched at step S705, whereby a video-level per-frame repetition/periodicity detection result is calculated. Each of the detected section is input, and the subtype (body or hand) of a stereotyped behavior is determined through binary classification using an AI-based stereotyped behavior recognition module at step S706. When the recognition result of the corresponding section is classified as a body usage action (whole-body action) at step S707, it is finally determined that a body stereotypy occurred.

When the recognition result is classified as an action using hands, whether a child is using an object is additionally determined at step S709 through zero-shot recognition based on a VLM at step S708. When it is determined that the child is not holding an object, it is finally determined that the child is doing a hand stereotypy. Conversely, when it is determined that the child is holding an object, it is finally determined that the child is doing a stereotyped behavior using the object, and the results of classification for the use of the object in the respective frames, which are obtained using the VLM, are clustered, whereby the result of detecting the section in which repetition/periodicity occurs is updated at step S710.

Figure 8:
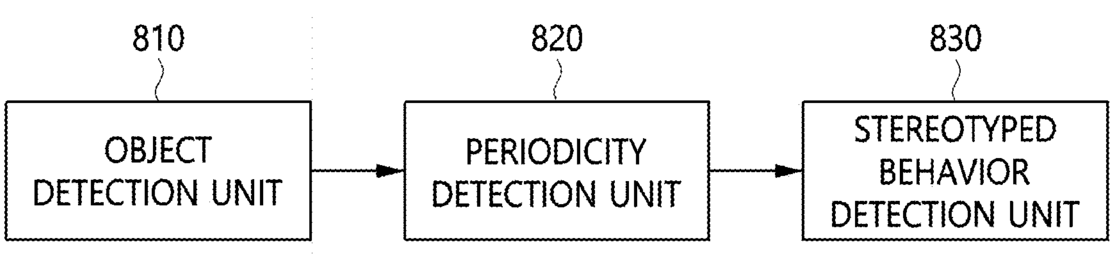
FIG. 8 is a block diagram illustrating an apparatus for stereotyped behavior detection for supporting ASD diagnosis according to an embodiment of the present disclosure.

FIG. 8 is a block diagram illustrating an apparatus for stereotyped behavior detection for supporting ASD diagnosis according to an embodiment of the present disclosure.

Referring to FIG. 8, the apparatus for stereotyped behavior detection for supporting ASD diagnosis according to an embodiment of the present disclosure includes an object detection unit 810 for detecting the target object to be assessed in an input video, a periodicity detection unit 820 for detecting a section in which a periodic behavior occurs using an image sequence of the target object, and a stereotyped behavior detection unit 830 for classifying a stereotyped behavior in the section in which the periodic behavior occurs.

Here, the periodicity detection unit 820 may detect a periodic behavior based on first dense sampling for the input video and detect a periodic behavior based on second dense sampling having a sampling stride that differs from that of the first dense sampling.

Here, the periodicity detection unit 820 may determine per-frame periodicity based on a self-similarity matrix generated based on the image sequence of the target object.

Here, the periodicity detection unit 820 may determine the final per-frame periodicity to be positive when both first per-frame periodicity determined based on the first dense sampling and second per-frame periodicity determined based on the second dense sampling have positive values.

Here, the stereotyped behavior may be classified as a body stereotypy or a hand stereotypy.

Here, when the stereotyped behavior is classified as a hand stereotypy, the stereotyped behavior detection unit 830 may determine whether the hand stereotypy is stereotyped use of an object using a Vision-Language Model (VLM).

Here, when it is determined that stereotyped use of an object is present, the periodicity detection unit 820 may update the section in which the periodic behavior occurs.

Here, the periodicity detection unit 820 may update the section in which the periodic behavior occurs by connecting frames including the object.

Here, the object detection unit 810 may detect a human area in the input video and detect a child area in the detected human area.

Figure 9:
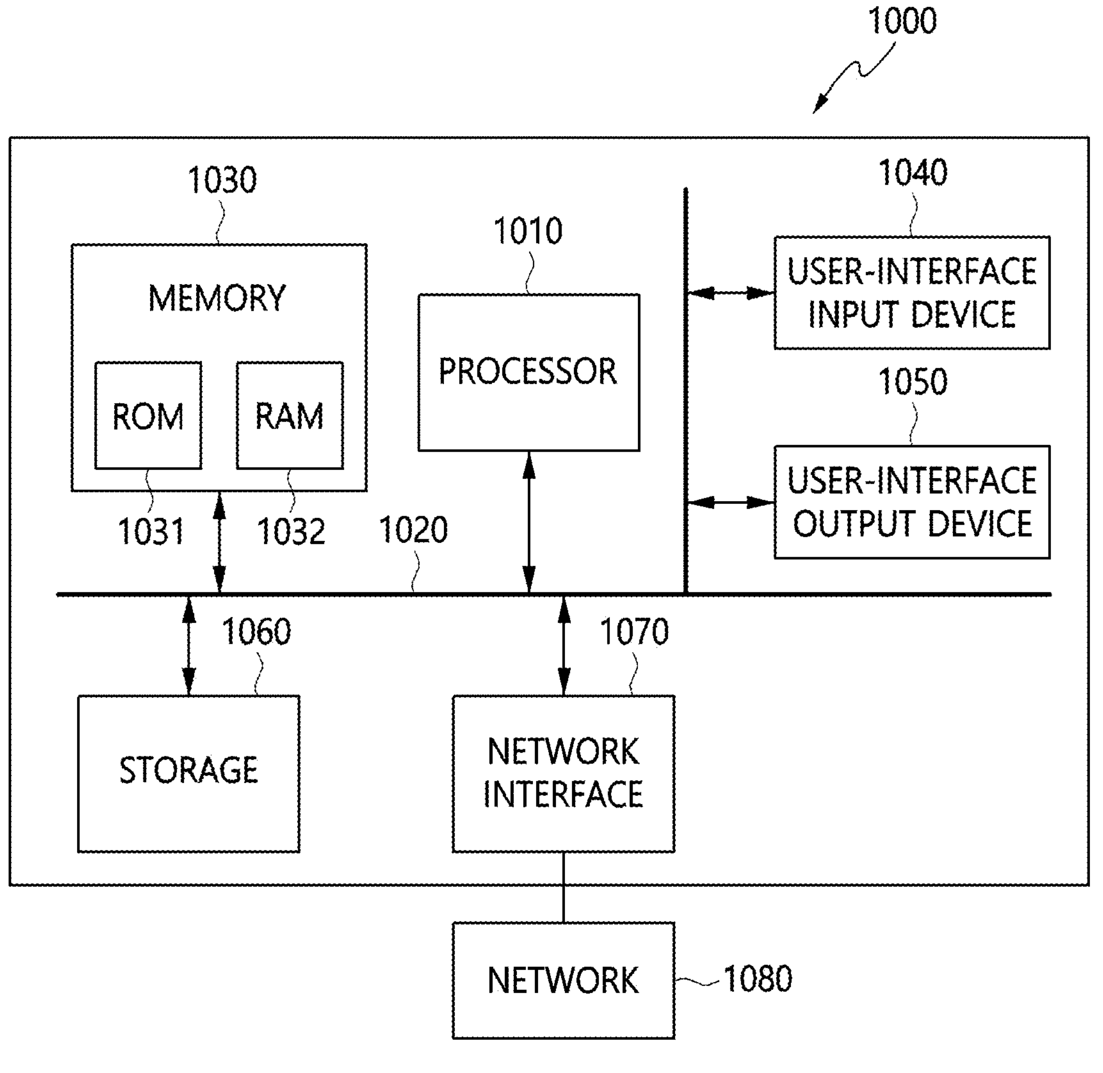
FIG. 9 is a view illustrating the configuration of a computer system according to an embodiment.

FIG. 9 is a view illustrating the configuration of a computer system according to an embodiment.

The apparatus for stereotyped behavior detection for supporting ASD diagnosis according to an embodiment may be implemented in a computer system 1000 including a computer-readable recording medium.

The computer system 1000 may include one or more processors 1010, memory 1030, a user-interface input device 1040, a user-interface output device 1050, and storage 1060, which communicate with each other via a bus 1020. Also, the computer system 1000 may further include a network interface 1070 connected with a network 1080. The processor 1010 may be a central processing unit or a semiconductor device for executing a program or processing instructions stored in the memory 1030 or the storage 1060. The memory 1030 and the storage 1060 may be storage media including at least one of a volatile medium, a non-volatile medium, a detachable medium, a non-detachable medium, a communication medium, or an information delivery medium, or a combination thereof. For example, the memory 1030 may include ROM 1031 or RAM 1032.

According to the disclosed embodiment, an integrated pipeline for stereotyped behavior detection is presented, and this may be used as diagnosis support technology for early screening of children with Autism Spectrum Disorder (ASD).

That is, the conventional AI-based technologies in the behavior recognition and behavior detection fields cannot ensure stable recognition and detection performance for types of behaviors other than behaviors predefined in a training dataset, but the present disclosure uses distinct characteristics of stereotyped behaviors, such as repetition and periodicity, thereby ensuring stable performance in detection of behavior occurrence sections even in open-set settings not present in the training dataset.

Also, according to the disclosed embodiment, in order to detect a section in which repetition and periodicity occur in a video, not uniform sampling but dense sampling is proposed along with a multi-stride-based sampling method, whereby stable performance may be ensured for detection of repetitive behaviors having different periods.

Also, the existing object detectors are able to detect only object types defined in a training dataset, but in the present disclosure, whether a child is holding an object in his or her hand is determined based on a zero-shot recognizer based on a Vision-Language Model (VLM), whereby an object usage stereotypy may be stably detected regardless of the types of objects.

Also, when an object usage stereotypy is finally detected, a method for improving performance by updating a repetitive section detection result by clustering the results based on the VLM is presented.

An integrated pipeline for detecting a stereotyped behavior is presented by integrating the above-mentioned methods. This may reduce time and cost incurred by relying on medical professionals, alleviate the reluctance to undergo diagnosis, easily support diagnosis through a system that can be easily installed in homes and childcare facilities, and provide fast access when analysis of video data for screening is attempted in medical institutions. Also, this may be used as technology for supporting early diagnosis that is crucial for prognosis of a child with ASD.

According to the present disclosure, an AI-based integrated method for stereotyped behavior detection for supporting diagnosis of children with ASD may be provided.

Also, the present disclosure may effectively detect repetitive and periodic stereotyped behaviors.

Also, the present disclosure may accurately detect subtypes of stereotyped behaviors.

Specific implementations described in the present disclosure are embodiments and are not intended to limit the scope of the present disclosure. For conciseness of the specification, descriptions of conventional electronic components, control systems, software, and other functional aspects thereof may be omitted. Also, lines connecting components or connecting members illustrated in the drawings show functional connections and/or physical or circuit connections, and may be represented as various functional connections, physical connections, or circuit connections that are capable of replacing or being added to an actual device. Also, unless specific terms, such as "essential", "important", or the like, are used, the corresponding components may not be absolutely necessary.

Accordingly, the spirit of the present disclosure should not be construed as being limited to the above-described embodiments, and the entire scope of the appended claims and their equivalents should be understood as defining the scope and spirit of the present disclosure.

What is claimed is:

1. A method for stereotyped behavior detection for supporting diagnosis of Autism Spectrum Disorder (ASD), comprising:

detecting a target object to be assessed in an input video;

detecting a section in which a periodic behavior occurs using an image sequence of the target object; and classifying a stereotyped behavior in the section in which the periodic behavior occurs, wherein detecting the section in which the periodic behavior occurs includes:

detecting a periodic behavior based on first dense sampling for the input video; and detecting a periodic behavior based on second dense sampling having a sampling stride that differs from that of the first dense sampling.

2. The method of claim 1, wherein detecting the section in which the periodic behavior occurs comprises determining per-frame periodicity based on a self-similarity matrix generated based on the image sequence of the target object.

3. The method of claim 1, wherein detecting the section in which the periodic behavior occurs comprises determining final per-frame periodicity to be positive when both first per-frame periodicity determined based on the first dense sampling and second per-frame periodicity determined based on the second dense sampling have positive values.

4. The method of claim 1, wherein the stereotyped behavior is classified as a body stereotypy or a hand stereotypy.

5. The method of claim 4, wherein classifying the stereotyped behavior comprises, when the stereotyped behavior is classified as a hand stereotypy, determining whether the hand stereotypy is stereotyped use of an object using a Vision-Language Model (VLM).

6. The method of claim 5, further comprising:

updating the section in which the periodic behavior occurs when it is determined that stereotyped use of an object is present.

7. The method of claim 6, wherein updating the section in which the periodic behavior occurs comprises updating the section in which the periodic behavior occurs by connecting frames including the object.

8. The method of claim 1, wherein detecting the target object includes detecting a human area in the input video; and detecting a child area in the detected human area.

9. An apparatus for stereotyped behavior detection for supporting diagnosis of Autism Spectrum Disorder (ASD), comprising:

a memory storing instructions; and one or more processors configured to execute the instructions to:

detect a target object to be assessed in an input video;

detect a section in which a periodic behavior occurs using an image sequence of the target object; and classify a stereotyped behavior in the section in which the periodic behavior occurs, wherein the one or more processors are configured to detect a periodic behavior based on first dense sampling for the input video and detect a periodic behavior based on second dense sampling having a sampling stride that differs from that of the first dense sampling.

10. The apparatus of claim 9, wherein the one or more processors are configured to determine per-frame periodicity based on a self-similarity matrix generated based on the image sequence of the target object.

11. The apparatus of claim 9, wherein the one or more processors are configured to determine final per-frame periodicity to be positive when both first per-frame periodicity determined based on the first dense sampling and second per-frame periodicity determined based on the second dense sampling have positive values.

12. The apparatus of claim 9, wherein the stereotyped behavior is classified as a body stereotypy or a hand stereotypy.

13. The apparatus of claim 12, wherein, when the stereotyped behavior is classified as a hand stereotypy, the one or more processors are configured to determine whether the hand stereotypy is stereotyped use of an object using a Vision-Language Model (VLM).

14. The apparatus of claim 13, wherein the one or more processors are configured to update the section in which the periodic behavior occurs when it determines that stereotyped use of an object is present.

15. The apparatus of claim 14, wherein the one or more processors are configured to update the section in which the periodic behavior occurs by connecting frames including the object.

16. The apparatus of claim 9, wherein the one or more processors are configured to detect a human area in the input video and detects a child area in the detected human area.

* * * * *